(12) United States Patent
Pigg

(10) Patent No.: US 10,299,966 B2
(45) Date of Patent: May 28, 2019

(54) REINFORCED ADHESIVE BACKING SHEET

(75) Inventor: William Pigg, Elvington (GB)

(73) Assignee: KCI USA, INC., San Antonio, TX (US)

( * ) Notice: Subject to any disclaimer, the term of this patent is extended or adjusted under 35 U.S.C. 154(b) by 13 days.

(21) Appl. No.: 12/810,119

(22) PCT Filed: Dec. 19, 2008

(86) PCT No.: PCT/GB2008/004216
§ 371 (c)(1),
(2), (4) Date: Sep. 21, 2010

(87) PCT Pub. No.: WO2009/081134
PCT Pub. Date: Jul. 2, 2009

(65) Prior Publication Data
US 2011/0004139 A1    Jan. 6, 2011

(30) Foreign Application Priority Data
Dec. 24, 2007    (GB) .................................... 0725215.8

(51) Int. Cl.
*A61L 15/58*    (2006.01)
*A61F 13/02*    (2006.01)
*A61F 13/00*    (2006.01)

(52) U.S. Cl.
CPC ........ *A61F 13/023* (2013.01); *A61F 13/0203* (2013.01); *A61F 2013/00263* (2013.01);
(Continued)

(58) Field of Classification Search
USPC ............ 442/286, 221; 428/304.4, 40.1, 41.5, 428/41.7, 42.1, 42.3, 137, 138; 602/54,
(Continued)

(56) References Cited

U.S. PATENT DOCUMENTS 1,355,846 A    10/1920 Rannells
2,547,758 A    4/1951 Kelling
(Continued)

FOREIGN PATENT DOCUMENTS

AU    550575 B2    3/1986
AU    745271 B2    3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery.
(Continued)

*Primary Examiner* — Ophelia A Hawthorne
(74) *Attorney, Agent, or Firm* — Foley & Lardner LLP

(57) ABSTRACT

A backing sheet for use in a wound dressing, comprising a semipermeable continuous film laminated to an adhesive-coated apertured layer, wherein the apertured layer comprises a solid substrate coated with a medically acceptable adhesive. Also provided is a method of making a backing sheet for use in a wound dressing, said method comprising the steps of: forming an adhesive-coated apertured layer by coating a medically acceptable adhesive onto an apertured solid substrate, followed by laminating the adhesive-coated apertured layer to a semipermeable continuous film.

13 Claims, 2 Drawing Sheets

(52) U.S. Cl.
CPC ............... *Y10T 428/24306* (2015.01); *Y10T 428/24322* (2015.01)

(58) Field of Classification Search
USPC ...................................... 602/41, 47, 52, 58
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,172,808 A | 3/1965 | Baumann et al. | |
| 3,367,332 A | 2/1968 | Groves | |
| 3,376,868 A | 4/1968 | Mondiadis | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,742,952 A | 7/1973 | Magers et al. | |
| 3,774,611 A | 11/1973 | Tussey et al. | |
| 3,777,016 A | 12/1973 | Gilbert | |
| 3,779,243 A | 12/1973 | Tussey et al. | |
| 3,826,254 A | 7/1974 | Mellor | |
| 3,852,823 A | 12/1974 | Jones | |
| 3,967,624 A | 7/1976 | Milnamow | |
| 3,983,297 A | 9/1976 | Ono et al. | |
| 4,080,970 A | 3/1978 | Miller | |
| 4,096,853 A | 6/1978 | Weigand | |
| 4,139,004 A | 2/1979 | Gonzalez, Jr. | |
| 4,141,361 A | 2/1979 | Snyder | |
| 4,163,822 A * | 8/1979 | Walter | 428/317.3 |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,360,015 A * | 11/1982 | Mayer | A61F 13/00029 602/42 |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,414,970 A * | 11/1983 | Berry | A61F 13/00038 602/75 |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,529,402 A | 7/1985 | Weilbacher et al. | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,652 A | 5/1987 | Weilbacher | |
| 4,664,662 A | 5/1987 | Webster | |
| 4,710,165 A | 12/1987 | McNeil et al. | |
| 4,715,857 A | 12/1987 | Juhasz et al. | |
| 4,733,659 A | 3/1988 | Edenbaum et al. | |
| 4,743,232 A | 5/1988 | Kruger | |
| 4,753,230 A | 6/1988 | Carus et al. | |
| 4,758,220 A | 7/1988 | Sundblom et al. | |
| 4,787,888 A | 11/1988 | Fox | |
| 4,826,494 A | 5/1989 | Richmond et al. | |
| 4,832,008 A | 5/1989 | Gilman | |
| 4,838,883 A | 6/1989 | Matsuura | |
| 4,840,187 A | 6/1989 | Brazier | |
| 4,848,364 A | 7/1989 | Bosman | |
| 4,863,449 A | 9/1989 | Therriault et al. | |
| 4,871,611 A | 10/1989 | LeBel | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,930,997 A | 6/1990 | Bennett | |
| 4,941,882 A | 7/1990 | Ward et al. | |
| 4,953,565 A | 9/1990 | Tachibana et al. | |
| 4,961,493 A | 10/1990 | Kaihatsu | |
| 4,969,880 A | 11/1990 | Zamierowski | |
| 4,981,474 A | 1/1991 | Bopp et al. | |
| 4,985,019 A | 1/1991 | Michelson | |
| 4,995,382 A | 2/1991 | Lang et al. | |
| 4,996,128 A | 2/1991 | Aldecoa et al. | |
| 5,010,883 A * | 4/1991 | Rawlings et al. | 602/52 |
| 5,018,515 A | 5/1991 | Gilman | |
| 5,037,397 A | 8/1991 | Kalt et al. | |
| 5,086,170 A | 2/1992 | Luheshi et al. | |
| 5,092,323 A | 3/1992 | Riedel et al. | |
| 5,092,858 A | 3/1992 | Benson et al. | |
| 5,100,396 A | 3/1992 | Zamierowski | |
| 5,112,323 A | 5/1992 | Winkler et al. | |
| 5,134,994 A | 8/1992 | Say | |
| 5,149,331 A | 9/1992 | Ferdman et al. | |
| 5,151,314 A | 9/1992 | Brown | |
| 5,152,757 A | 10/1992 | Eriksson | |
| 5,167,613 A | 12/1992 | Karami et al. | |
| 5,176,663 A | 1/1993 | Svedman et al. | |
| 5,180,375 A | 1/1993 | Feibus | |
| 5,215,522 A | 6/1993 | Page et al. | |
| 5,232,453 A | 8/1993 | Plass et al. | |
| 5,261,893 A | 11/1993 | Zamierowski | |
| 5,266,372 A | 11/1993 | Arakawa et al. | |
| 5,270,358 A | 12/1993 | Asmus | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,329 A | 8/1994 | Croquevielle | |
| 5,342,376 A | 8/1994 | Ruff | |
| 5,344,415 A | 9/1994 | DeBusk et al. | |
| 5,356,386 A | 10/1994 | Goldberg et al. | |
| 5,358,494 A | 10/1994 | Svedman | |
| 5,384,174 A * | 1/1995 | Ward et al. | 428/41.5 |
| 5,387,207 A | 2/1995 | Dyer et al. | |
| 5,419,769 A | 5/1995 | Devlin et al. | |
| 5,423,778 A | 6/1995 | Eriksson et al. | |
| 5,429,590 A | 7/1995 | Saito et al. | |
| 5,437,622 A | 8/1995 | Carion | |
| 5,437,651 A | 8/1995 | Todd et al. | |
| 5,445,604 A * | 8/1995 | Lang | A61F 13/00046 602/47 |
| 5,447,492 A | 9/1995 | Cartmell et al. | |
| 5,501,212 A | 3/1996 | Psaros | |
| 5,522,808 A | 6/1996 | Skalla | |
| 5,527,293 A | 6/1996 | Zamierowski | |
| 5,549,584 A | 8/1996 | Gross | |
| 5,549,585 A | 8/1996 | Maher et al. | |
| 5,556,375 A | 9/1996 | Ewall | |
| 5,585,178 A | 12/1996 | Calhoun et al. | |
| 5,599,292 A | 2/1997 | Yoon | |
| 5,607,388 A | 3/1997 | Ewall | |
| 5,634,893 A | 6/1997 | Rishton | |
| 5,636,643 A | 6/1997 | Argenta et al. | |
| 5,641,506 A | 6/1997 | Talke et al. | |
| 5,645,081 A | 7/1997 | Argenta et al. | |
| 5,653,224 A | 8/1997 | Johnson | |
| 5,678,564 A | 10/1997 | Lawrence et al. | |
| 5,710,233 A | 1/1998 | Meckel et al. | |
| 5,714,225 A | 2/1998 | Hansen et al. | |
| 5,736,470 A | 4/1998 | Schneberger et al. | |

(56) References Cited

U.S. PATENT DOCUMENTS

| | | |
|---|---|---|
| 5,776,119 A | 7/1998 | Bilbo et al. |
| 5,807,295 A * | 9/1998 | Hutcheon et al. ............... 602/42 |
| 5,919,476 A | 7/1999 | Fischer et al. |
| 5,941,863 A | 8/1999 | Guidotti et al. |
| 5,981,822 A | 11/1999 | Addison |
| 6,071,267 A | 6/2000 | Zamierowski |
| 6,086,995 A | 7/2000 | Smith |
| 6,135,116 A | 10/2000 | Vogel et al. |
| 6,174,306 B1 | 1/2001 | Fleischmann |
| 6,191,335 B1 * | 2/2001 | Robinson ......................... 602/42 |
| 6,241,747 B1 | 6/2001 | Ruff |
| 6,262,329 B1 * | 7/2001 | Brunsveld et al. .............. 602/54 |
| 6,287,316 B1 | 9/2001 | Agarwal et al. |
| 6,345,623 B1 | 2/2002 | Heaton et al. |
| 6,458,109 B1 | 10/2002 | Henley et al. |
| 6,488,643 B1 | 12/2002 | Tumey et al. |
| 6,493,568 B1 | 12/2002 | Bell et al. |
| 6,495,229 B1 * | 12/2002 | Carte ................... A61F 13/023 428/137 |
| 6,548,727 B1 * | 4/2003 | Swenson ......................... 602/41 |
| 6,553,998 B2 | 4/2003 | Heaton et al. |
| 6,566,575 B1 | 5/2003 | Stickels et al. |
| 6,566,577 B1 | 5/2003 | Addison et al. |
| 6,626,891 B2 | 9/2003 | Ohmstede |
| 6,627,215 B1 | 9/2003 | Dale et al. |
| 6,648,862 B2 | 11/2003 | Watson |
| 6,680,113 B1 | 1/2004 | Lucast et al. |
| 6,685,681 B2 | 2/2004 | Lockwood et al. |
| 6,693,180 B2 | 2/2004 | Lee et al. |
| 6,695,823 B1 | 2/2004 | Lina et al. |
| 6,752,794 B2 | 6/2004 | Lockwood et al. |
| 6,787,682 B2 * | 9/2004 | Gilman ................. A61F 13/023 602/42 |
| 6,814,079 B2 | 11/2004 | Heaton et al. |
| 6,855,135 B2 | 2/2005 | Lockwood et al. |
| 6,856,821 B2 | 2/2005 | Johnson |
| 6,979,324 B2 | 12/2005 | Bybordi et al. |
| 7,070,584 B2 | 7/2006 | Johnson et al. |
| 7,154,017 B2 | 12/2006 | Sigurjonsson et al. |
| 7,402,721 B2 | 7/2008 | Sigurjonsson et al. |
| 7,569,742 B2 | 8/2009 | Haggstrom et al. |
| 7,645,269 B2 | 1/2010 | Zamierowski |
| 8,058,499 B2 * | 11/2011 | Silcock ............... A61F 13/0203 602/41 |
| 8,298,197 B2 | 10/2012 | Eriksson et al. |
| 8,529,532 B2 | 9/2013 | Pinto et al. |
| 8,632,523 B2 | 1/2014 | Eriksson et al. |
| 8,764,732 B2 | 7/2014 | Hartwell |
| 9,192,444 B2 | 11/2015 | Locke et al. |
| 2001/0030304 A1 | 10/2001 | Kohda et al. |
| 2001/0051178 A1 | 12/2001 | Blatchford et al. |
| 2002/0009568 A1 | 1/2002 | Bries et al. |
| 2002/0016346 A1 | 2/2002 | Brandt et al. |
| 2002/0065494 A1 | 5/2002 | Lockwood et al. |
| 2002/0077661 A1 | 6/2002 | Saadat |
| 2002/0115951 A1 | 8/2002 | Norstrem et al. |
| 2002/0119292 A1 | 8/2002 | Venkatasanthanam et al. |
| 2002/0120185 A1 | 8/2002 | Johnson |
| 2002/0130064 A1 | 9/2002 | Adams et al. |
| 2002/0143286 A1 | 10/2002 | Tumey |
| 2002/0150270 A1 | 10/2002 | Werner |
| 2002/0150720 A1 | 10/2002 | Howard et al. |
| 2002/0161346 A1 | 10/2002 | Lockwood et al. |
| 2002/0164346 A1 | 11/2002 | Nicolette |
| 2002/0183702 A1 | 12/2002 | Henley et al. |
| 2002/0198504 A1 | 12/2002 | Risk et al. |
| 2003/0014022 A1 | 1/2003 | Lockwood et al. |
| 2003/0109855 A1 | 6/2003 | Solem et al. |
| 2003/0158577 A1 | 8/2003 | Ginn et al. |
| 2003/0212357 A1 | 11/2003 | Pace |
| 2003/0225347 A1 | 12/2003 | Argenta et al. |
| 2003/0225355 A1 | 12/2003 | Butler |
| 2004/0002676 A1 * | 1/2004 | Siegwart et al. ............... 602/58 |
| 2004/0030304 A1 | 2/2004 | Hunt et al. |
| 2004/0064132 A1 | 4/2004 | Boehringer et al. |
| 2004/0077984 A1 | 4/2004 | Worthley |
| 2004/0099268 A1 | 5/2004 | Smith et al. |
| 2004/0118401 A1 | 6/2004 | Smith et al. |
| 2004/0127836 A1 | 7/2004 | Sigurjonsson et al. |
| 2004/0127862 A1 | 7/2004 | Bubb et al. |
| 2004/0133143 A1 | 7/2004 | Burton et al. |
| 2004/0186239 A1 | 9/2004 | Qin et al. |
| 2004/0219337 A1 | 11/2004 | Langley et al. |
| 2004/0230179 A1 | 11/2004 | Shehada |
| 2005/0034731 A1 | 2/2005 | Rousseau et al. |
| 2005/0054998 A1 | 3/2005 | Poccia et al. |
| 2005/0059918 A1 | 3/2005 | Sigurjonsson et al. |
| 2005/0065484 A1 | 3/2005 | Watson |
| 2005/0070858 A1 | 3/2005 | Lockwood et al. |
| 2005/0101940 A1 | 5/2005 | Radl et al. |
| 2005/0113732 A1 | 5/2005 | Lawry |
| 2005/0124925 A1 | 6/2005 | Scherpenborg |
| 2005/0131327 A1 | 6/2005 | Lockwood et al. |
| 2005/0137539 A1 | 6/2005 | Biggie et al. |
| 2005/0143694 A1 | 6/2005 | Schmidt et al. |
| 2005/0159695 A1 | 7/2005 | Cullen et al. |
| 2005/0161042 A1 | 7/2005 | Fudge et al. |
| 2005/0163978 A1 | 7/2005 | Strobech et al. |
| 2005/0214376 A1 | 9/2005 | Faure et al. |
| 2005/0233072 A1 | 10/2005 | Stephan et al. |
| 2005/0256437 A1 | 11/2005 | Silcock et al. |
| 2005/0261642 A1 | 11/2005 | Weston |
| 2005/0261643 A1 | 11/2005 | Bybordi et al. |
| 2005/0277860 A1 | 12/2005 | Jensen |
| 2006/0079852 A1 | 4/2006 | Bubb et al. |
| 2006/0083776 A1 | 4/2006 | Bott et al. |
| 2006/0154546 A1 * | 7/2006 | Murphy ................ A61F 13/023 442/286 |
| 2006/0241542 A1 | 10/2006 | Gudnason et al. |
| 2006/0271020 A1 | 11/2006 | Huang et al. |
| 2007/0027414 A1 | 2/2007 | Hoffman et al. |
| 2007/0078366 A1 | 4/2007 | Haggstrom et al. |
| 2007/0185426 A1 | 8/2007 | Ambrosio et al. |
| 2007/0225663 A1 | 9/2007 | Watt et al. |
| 2007/0265585 A1 | 11/2007 | Joshi et al. |
| 2007/0265586 A1 | 11/2007 | Joshi et al. |
| 2008/0090085 A1 | 4/2008 | Kawate et al. |
| 2008/0119802 A1 | 5/2008 | Riesinger |
| 2008/0149104 A1 | 6/2008 | Eifler |
| 2008/0195017 A1 | 8/2008 | Robinson et al. |
| 2008/0225663 A1 | 9/2008 | Smith et al. |
| 2008/0243044 A1 | 10/2008 | Hunt et al. |
| 2008/0269657 A1 | 10/2008 | Brenneman et al. |
| 2008/0271804 A1 | 11/2008 | Biggie et al. |
| 2009/0025724 A1 | 1/2009 | Herron, Jr. |
| 2009/0088719 A1 | 4/2009 | Driskell |
| 2009/0093779 A1 | 4/2009 | Riesinger |
| 2009/0124988 A1 | 5/2009 | Coulthard |
| 2009/0177172 A1 | 7/2009 | Wilkes |
| 2009/0216204 A1 | 8/2009 | Bhavaraju et al. |
| 2009/0227969 A1 | 9/2009 | Jaeb et al. |
| 2009/0264807 A1 | 10/2009 | Haggstrom et al. |
| 2009/0292264 A1 | 11/2009 | Hudspeth et al. |
| 2009/0312662 A1 | 12/2009 | Colman et al. |
| 2009/0326488 A1 | 12/2009 | Budig et al. |
| 2010/0063467 A1 | 3/2010 | Addison et al. |
| 2010/0106106 A1 | 4/2010 | Heaton et al. |
| 2010/0106118 A1 | 4/2010 | Heaton et al. |
| 2010/0125259 A1 | 5/2010 | Olson |
| 2010/0159192 A1 | 6/2010 | Cotton |
| 2010/0185163 A1 | 7/2010 | Heagle |
| 2010/0226824 A1 | 9/2010 | Ophir et al. |
| 2010/0262090 A1 | 10/2010 | Riesinger |
| 2010/0267302 A1 | 10/2010 | Kantner et al. |
| 2010/0305490 A1 | 12/2010 | Coulthard et al. |
| 2010/0305524 A1 | 12/2010 | Vess et al. |
| 2010/0324516 A1 | 12/2010 | Braga et al. |
| 2011/0046585 A1 | 2/2011 | Weston |
| 2011/0137271 A1 | 6/2011 | Andresen et al. |
| 2011/0160686 A1 * | 6/2011 | Ueda ................... A61F 13/0203 604/365 |
| 2011/0171480 A1 | 7/2011 | Mori et al. |
| 2011/0172617 A1 | 7/2011 | Riesinger |
| 2011/0224631 A1 | 9/2011 | Simmons et al. |

(56) References Cited

U.S. PATENT DOCUMENTS

| | | |
|---|---|---|
| 2011/0229688 A1 | 9/2011 | Cotton |
| 2011/0244010 A1 | 10/2011 | Doshi |
| 2011/0257617 A1 | 10/2011 | Franklin |
| 2012/0016322 A1 | 1/2012 | Coulthard et al. |
| 2012/0123359 A1 | 5/2012 | Reed |
| 2012/0143157 A1 | 6/2012 | Riesinger |
| 2012/0258271 A1 | 10/2012 | Maughan |
| 2013/0030394 A1 | 1/2013 | Locke et al. |
| 2013/0066285 A1 | 3/2013 | Locke et al. |
| 2013/0096518 A1 | 4/2013 | Hall et al. |
| 2013/0152945 A1 | 6/2013 | Locke et al. |
| 2014/0039423 A1 | 2/2014 | Riesinger |
| 2014/0039424 A1 | 2/2014 | Locke |
| 2014/0155849 A1 | 6/2014 | Heaton et al. |
| 2014/0171851 A1 | 6/2014 | Addison |
| 2014/0309574 A1 | 10/2014 | Cotton |
| 2014/0350494 A1 | 11/2014 | Hartwell et al. |
| 2015/0030848 A1 | 1/2015 | Goubard |
| 2015/0119830 A1 | 4/2015 | Luckemeyer et al. |
| 2015/0190286 A1 | 7/2015 | Allen et al. |
| 2016/0067107 A1 | 3/2016 | Cotton |

FOREIGN PATENT DOCUMENTS

| | | |
|---|---|---|
| AU | 755496 B2 | 12/2002 |
| AU | 2009200608 A1 | 10/2009 |
| CA | 2005436 A1 | 6/1990 |
| CN | 87101823 A | 8/1988 |
| DE | 26 40 413 A1 | 3/1978 |
| DE | 43 06 478 A1 | 9/1994 |
| DE | 29 504 378 U1 | 9/1995 |
| DE | 202004018245 U1 | 7/2005 |
| EP | 0097517 A1 | 1/1984 |
| EP | 0100148 A1 | 2/1984 |
| EP | 0117632 A2 | 9/1984 |
| EP | 0 147 119 | 7/1985 |
| EP | 0161865 A2 | 11/1985 |
| EP | 0251810 A2 | 1/1988 |
| EP | 0275353 A2 | 7/1988 |
| EP | 0358302 A2 | 3/1990 |
| EP | 0 538 917 | 4/1993 |
| EP | 0538917 A1 | 4/1993 |
| EP | 0 630 629 | 12/1994 |
| EP | 0630629 A1 | 12/1994 |
| EP | 0659390 A2 | 6/1995 |
| EP | 0633758 B1 | 10/1996 |
| EP | 1002846 A1 | 5/2000 |
| EP | 1018967 A1 | 7/2000 |
| EP | 2578193 A1 | 4/2013 |
| GB | 692578 A | 6/1953 |
| GB | 1386800 A | 3/1975 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| GB | 2377939 A | 1/2003 |
| GB | 2392836 A | 3/2004 |
| GB | 2393655 A | 4/2004 |
| GB | 2425487 A | 11/2006 |
| GB | 2452720 A | 3/2009 |
| GB | 2496310 A | 5/2013 |
| JP | 1961003393 | 2/1961 |
| JP | S62139523 U | 9/1987 |
| JP | S62-275456 A | 11/1987 |
| JP | 2007254515 A | 10/2007 |
| JP | 2008080137 A | 4/2008 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 8707164 A1 | 12/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 9622753 A1 | 8/1996 |
| WO | 97/18007 A1 | 5/1997 |
| WO | 99/13793 A1 | 3/1999 |
| WO | 99/65542 A1 | 12/1999 |
| WO | 0119306 | 3/2001 |
| WO | 01/36188 A1 | 5/2001 |
| WO | 01/60296 A1 | 8/2001 |
| WO | 0168021 A1 | 9/2001 |
| WO | 0185248 A1 | 11/2001 |
| WO | 0243743 A1 | 6/2002 |
| WO | 02062403 A1 | 8/2002 |
| WO | 03-018098 A2 | 3/2003 |
| WO | 03045294 A1 | 6/2003 |
| WO | 03045492 A1 | 6/2003 |
| WO | 03053484 A1 | 7/2003 |
| WO | 2004024197 A1 | 3/2004 |
| WO | 2004037334 A1 | 5/2004 |
| WO | 2004112852 A1 | 12/2004 |
| WO | 2005002483 | 1/2005 |
| WO | 2005062896 A2 | 7/2005 |
| WO | 2005105176 A1 | 11/2005 |
| WO | 2005123170 A1 | 12/2005 |
| WO | 2007022097 | 2/2007 |
| WO | 2007030601 A2 | 3/2007 |
| WO | 2007070269 A1 | 6/2007 |
| WO | 2007085396 A1 | 8/2007 |
| WO | 2007087811 A1 | 8/2007 |
| WO | 2007113597 A2 | 10/2007 |
| WO | 2007133618 A2 | 11/2007 |
| WO | 2008041926 A1 | 4/2008 |
| WO | 2008054312 A1 | 5/2008 |
| WO | 2008/082444 A2 | 7/2008 |
| WO | 2008/100440 A1 | 8/2008 |
| WO | 2008104609 A1 | 9/2008 |
| WO | 2008/131895 A1 | 11/2008 |
| WO | 2009/002260 A1 | 12/2008 |
| WO | 2008149107 A1 | 12/2008 |
| WO | 2009066105 A1 | 5/2009 |
| WO | 2009066106 A1 | 5/2009 |
| WO | 2009081134 A1 | 7/2009 |
| WO | 2009089016 A1 | 7/2009 |
| WO | 2009/124100 A1 | 10/2009 |
| WO | 2009126103 A1 | 10/2009 |
| WO | 2010032728 A1 | 3/2010 |
| WO | 2010/056977 A2 | 5/2010 |
| WO | 2010129299 A2 | 11/2010 |
| WO | 2011008497 A2 | 1/2011 |
| WO | 2011/049562 A1 | 4/2011 |
| WO | 2011043786 A1 | 4/2011 |
| WO | 2011115908 A1 | 9/2011 |
| WO | 2011121127 A1 | 10/2011 |
| WO | 2011162862 A1 | 12/2011 |
| WO | 2012/112204 A1 | 8/2012 |
| WO | 2012104584 A1 | 8/2012 |
| WO | 2012140378 A1 | 10/2012 |
| WO | 2012143665 A1 | 10/2012 |
| WO | 2013009239 A1 | 1/2013 |
| WO | 2013090810 A1 | 6/2013 |
| WO | 2014039557 A1 | 3/2014 |
| WO | 2014/113253 A1 | 7/2014 |
| WO | 2014140608 A1 | 9/2014 |
| WO | 2014143488 A1 | 9/2014 |
| WO | 2015/065615 A1 | 5/2015 |
| WO | 2015130471 A1 | 9/2015 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

(56) References Cited

OTHER PUBLICATIONS

John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinoviʔ, V. ʔukiʔ, Ž. Maksimoviʔ, ʔ. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
European Examination Report dated Jun. 29, 2016, corresponding to EP Application No. 16173614.5.
International Search Report and Written Opinion for PCT/GB2008/004216 dated Jul. 2, 2009.
International Search Report and Written Opinion for PCT/GB2008/003075 dated Mar. 11, 2010.
International Search Report and Written Opinion for PCT/GB2012/000099 dated May 2, 2012.
EP Examination Report for corresponding application 12705381.7, dated May 22, 2014.
International Search Report and Written Opinion for PCT/US2012/069893 dated Apr. 8, 2013.
International Search Report and Written Opinion for PCT/US2013/070070 dated Jan. 29, 2014.
International Search Report and Written Opinion for PCT/US2014/016320 dated Apr. 15, 2014.
International Search Report and Written Opinion for PCT/US2014/056566 dated Dec. 5, 2014.
International Search Report and Written Opinion for PCT/US2014/056508 dated Dec. 9, 2014.
International Search Report and Written Opinion for PCT/US2014/056524 dated Dec. 11, 2014.
International Search Report and Written Opinion for PCT/US2014/056594 dated Dec. 2, 2014.
Partial Internationl Search Report dated Jul. 31, 2009; PCT Internationl Application No. PCT/US2009/036222.
International Search Report and Written opinion dated Dec. 15, 2009; PCT Internation Application No. PCT/US2009/036222.

(56) References Cited

OTHER PUBLICATIONS

International Search Report and Written Opinion dated Feb. 24, 2010; PCT/US2009/057182.
International Search Report and Written Opinion dated Jan. 5, 2010; PCT International Application No. PCT/US2009/057130.
Response filed Oct. 20, 2011 for U.S. Appl. No. 12/398,904.
Interview Summary dated Oct. 27, 2011 for U.S. Appl. No. 12/398,904.
Non-Final Office Action dated Jul. 20, 2011 for U.S. Appl. No. 12/398,904.
NDP 1000 Negative Pressure Wound Terapy System, Kalypto Medical, pp. 1-4.
Partial International Search Report dated Jul. 31, 2009 for PCT International Application No. PCT/US2009/036217.
International Search Report and Written Opinion dated May 31, 2010 for PCT Application No. PCT/US2009/064364.
Examination report for AU2009221772 dated Apr. 4, 2011.
Response filed Oct. 21, 2011 for U.S. Appl. No. 12/398,891.
Interview Summary dated Oct. 27, 2011 for U.S. Appl. No. 12/398,891.
Restriction Requirement dated Jun. 13, 2011 for U.S. Appl. No. 12/398,891.
Response filed Jun. 24, 2011 for U.S. Appl. No. 12/398,891.
Non-Final Office Action dated Jul. 21, 2011 for U.S. Appl. No. 12/398,891.
International Search Report and Written Opinion dated Oct. 19, 2010; PCT International Application No. PCT/US2009/036217.
International Search Report and Written Opinion dated Feb. 24, 2010; PCT International Application No. PCT/US2009/057182.
NPD 1000 Negative Pressure Would Therapy System, Kalypto Medical, pp. 1-4.
Partial International Search Report dated Jul. 31, 2009; PCT Internationl Application No. PCT/US2009/036222.
Non-Final Rejection for U.S. Appl. No. 12/398,904 dated Mar. 14, 2012.
Response to Non-Final Rejection for U.S. Appl. No. 12/398,904, filed Jun. 4, 2012.
International Search Report and Written Opinion for PCT/US2014/061251 dated May 8, 2015.
International Search Report and Written Opinion for PCT/IB2013/060862 dated Jun. 26, 2014.
International Search Report and Written Opinion for PCT/US2015/015493 dated May 4, 2015.
European Search Report for corresponding Application No. 15194949.2.
European Search Report for corresponding EPSN 15157408.4 published on Sep. 30, 2015.
International Search Report and Written Opinion for PCT/US2015/034289 dated Aug. 21, 2015.
International Search Report and Written Opinion for PCT/US2015/065135 dated Apr. 4, 2016.
International Search Report and Written Opinion for PCT/GB2012/050822 dated Aug. 8, 2012.
International Search Report and Written Opinion for PCT/US2015/029037 dated Sep. 4, 2015.
International Search Report and Written Opinion dated Jun. 1, 2011 for PCT International Application No. PCT/US2011/028344.
European Search Report for EP 11714148.1, dated May 2, 2014.
European Search Report for corresponding Application No. 15192606.0 dated Feb. 24, 2016.
International Search Report and Written Opinion for corresponding PCT/US2014/048081 dated Nov. 14, 2014.
International Search Report and Written Opinion for corresponding PCT/US2014/010704 dated Mar. 25, 2014.
European Search Report for corresponding EP Application 171572787 dated Jun. 6, 2017.
International Search Report and Written Opinion for corresponding application PCT/US2016/031397, dated Aug. 8, 2016.
European Search Report for corresponding application 17167872.5, dated Aug. 14, 2017.
M. Waring et al., "Cell attachment to adhesive dressing: qualitative and quantitative analysis", Wounds, UK, (2008), vol. 4, No. 3, pp. 35-47.
R. White, "Evidence for atraumatic soft silicone wound dressing use". Wound, UK (2005), vol. 3, pp. 104-108, Mepilex Border docs, (2001).
European Search Report for corresponding application 17183683.6, dated Sep. 18, 2017.
European Search Report for corresponding application 17164033.7, dated Oct. 13, 2017.
Extended European Search Report for corresponding application 17191970.7, dated Oct. 26, 2017.
Japanese office action for corresponding Japanese patent application 2015-547246, dated Sep. 5, 2017.

* cited by examiner

REINFORCED ADHESIVE BACKING SHEET

CROSS-REFERENCE TO RELATED APPLICATIONS

This application is a U.S. National Stage Patent Application of International Application No. PCT/GB2008/004216, filed Dec. 19, 2008, which claims priority to GB 0725215.8, filed on Dec. 24, 2007, both of which are incorporated herein by reference in their entirety.

STATEMENT REGARDING FEDERALLY SPONSORED RESEARCH OR DEVELOPMENT

Not Applicable

REFERENCE TO A "SEQUENCE LISTING

Not Applicable

FIELD OF THE INVENTION

The present invention relates to a reinforced adhesive backing sheet, to methods of making such backing sheets, and to wound dressings comprising such backing sheets.

BACKGROUND OF THE INVENTION

Many wound dressings comprise a wound contacting portion and a microorganism-impermeable backing sheet that covers the wound contacting portion. The wound-contacting portion, which may comprise several layers, is typically absorbent and may be therapeutic. In use, the backing sheet holds the wound contacting portion of the dressing in contact with the wound, blocks the ingress of microorganisms to the wound, and also prevents leakage of wound exudates from the dressing. In certain embodiments, the backing sheet is substantially coterminous with the wound contacting portion. In other embodiments, the backing sheet is larger than the wound contacting portion, such that a margin having width 1 mm to 50 mm, suitably 5 mm to 20 mm, extends around the wound contacting portion to form a so-called island dressing.

Conventional polymers for forming the backing sheet include polyurethanes and poly alkoxyalkyl acrylates and methacrylates such as those disclosed in GB-A-1280631. Typically, the backing sheet comprises a continuous sheet of a high density blocked polyurethane foam that is predominantly closed-cell. Well known backing sheet materials include the polyurethane films available under the Registered Trade Mark ESTANE.

The backing sheet is frequently coated with a medically acceptable adhesive to bond the backing sheet to the wound contacting portion, and/or to the skin of a patient around the wound. For example, in typical embodiments the backing sheet is adhesive coated at least in a marginal region thereof. As previously described, the backing sheet suitably extends beyond the outer edges of the wound contacting sheet to provide an adhesive-coated margin around the wound contacting sheet for attachment of the dressing to skin around a wound. The adhesive material can be moisture vapour transmitting, for example it may be a hydrogel adhesive. However, the more commonly used pressure-sensitive adhesives are not moisture vapour transmitting. These adhesives are typically printed onto the backing sheet in a patterned (discontinuous) fashion to allow passage of water vapour through the adhesive layer. The step of printing the adhesive adds expense and complexity to the manufacturing process.

Existing adhesive-coated backing sheets are generally quite thick. This thickness is needed in order to give the sheet sufficient stiffness for convenient handling prior to application to the wound. The adhesive layer is also typically quite thick, for example 100 to 250 $g/m^2$. Where a polyurethane foam backing sheet is used, the adhesive layer should be continuous in order to provide the necessary barrier to microorganisms. These thick materials are relatively expensive, and render the desired oxygen- and moisture-permeability difficult to achieve.

Accordingly, a need exists for adhesive backing sheets for use in wound dressings that combine the advantages of low cost, sufficient stiffness for easy handling, and high moisture vapour permeability.

SUMMARY OF THE INVENTION

In a first aspect, the present invention provides a backing sheet for use in a wound dressing, comprising a semipermeable continuous film laminated to an adhesive-coated aperture layer, wherein the aperture layer comprises a solid substrate coated with a medically acceptable adhesive.

In a second aspect, the present invention provides a wound dressing comprising a backing sheet according to the first aspect.

In a third aspect, the present invention provides a method of making a backing sheet for use in a wound dressing, said method comprising the steps of: forming an adhesive-coated apertured layer by coating a medically acceptable adhesive onto an apertured solid substrate, followed by laminating the adhesive-coated apertured layer to a semipermeable continuous film.

DETAILED DESCRIPTION OF THE INVENTION

Figure 1:
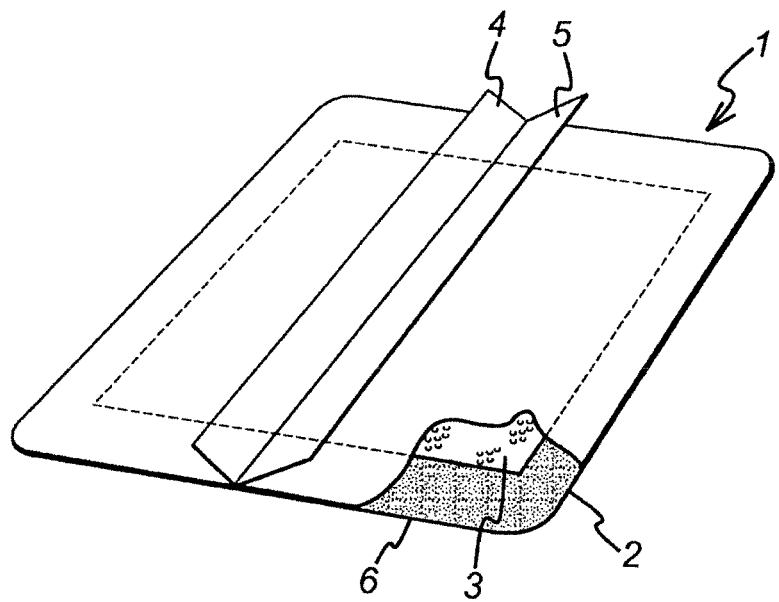
FIG. 1 shows a detail view of part of a backing sheet according to the invention.

The adhesive-coated apertured layer provides stiffness to the backing sheets of the present invention, so that thinner and thus more permeable continuous backing films can be used while maintaining acceptable handling properties. In addition, the lamination of the adhesive-coated apertured layer to the continuous film is simpler than many conventional adhesive coating processes, and allows smaller amounts of adhesive to be used. The adhesive-coated layer is apertured. That is to say, there are apertures in the adhesive-coated layer that are substantially adhesive-free and thereby maintain the moisture- and gas-permeability of the backing sheet, in particular when the adhesive is a conventional medically acceptable pressure sensitive adhesive (i.e. not a hydrogel adhesive).

The term "backing sheet" refers to a flexible, sheet material having a structure that is substantially continuous (on a cm scale) so that it can be cut to size to form the outer layer of a wound dressing.

The terms "laminated" and "laminating" refer to bonding of the apertured layer to a surface of the continuous film.

Suitably, the bonding is adhesive bonding by means of the adhesive coating on the apertured layer. Suitably, the bonding of the apertured layer to the continuous film is substantially solely by means of said adhesive coating. Suitably, the apertured layer is bonded to the backing sheet over substantially the whole of one side of the apertured layer, i.e. at least about 90% of the area of the apertured layer on one side, is bonded to the backing sheet. Suitably, the continuous film and the apertured adhesive-coated layer are substantially coterminous and bonded together across the whole of their respective areas. This results in a unitary, laminated backing sheet. The laminated backing sheets of the present invention are therefore quite different from conventional wound dressings that may have an apertured, adhesive-coated top sheet bonded to a backing sheet around a margin.

The terms "coated" and "coating" refer to application of a layer of adhesive to the apertured substrate. Suitably, substantially all surfaces of the solid substrate are coated with the same adhesive, for example by dipping the substrate in a liquid adhesive. In other embodiments, front and back surfaces of the solid substrate are coated with adhesive, for example by spraying. Suitably, substantially the whole of the side of the apertured substrate (excluding the apertures) facing the continuous film is coated with adhesive, so as to achieve bonding between the continuous film and the apertured sheet across the whole of that side of the apertured substrate. However, the apertures of the coated substrate are not completely filled with the adhesive, whereby apertures remain in the coated substrate to allow passage of gases.

Suitably, the semipermeable continuous film has a thickness in the range of from about 10 micrometers to about 200 micrometers, for example from about 20 micrometers to about 75 micrometers. In one embodiment, the semipermeable continuous film will have a moisture vapor transmission rate (MVTR) of about 300 to about 5000 $g/m^2/24$ hrs, for example about 500 to about 2000 $g/m^2/24$ hrs at 37.5° C. at 100% to 10% relative humidity difference and 32° C. by ASTM Standard E96-80. Suitable films include Smith & Nephew extruded medical films (EU31, EU65, EU93, EU110, PBA73, PBA105, BNX75) all of which are Polyurethane or polyurethane blends except for BNX75, which is a Polyethylene. Further suitable films are provided by Omniflex USA manufactured from TPU, and breathable films such as Inspire 2301 from Intellicoat and Amitel VT3801 from DSM. Suitable foam backing layers are provided by SCAPA and Rogers Corp.

The solid substrate of the apertured layer is suitably a layer or sheet having a low basis weight and thickness. For example, the basis weight may be from about 10 gsm to about 500 gsm, typically from about 20 gsm to about 300 gsm. In certain embodiments, the substrate has apertures arranged in a regular pattern, whereby after coating the apertures retain sufficient open (adhesive-free) area to mimic the use of a printed adhesive layer and allow transport of moisture vapour through the backing layer. Suitably, the apertured layer is laminated across substantially the whole of one surface of the film layer. The adhesive suitably also bonds the apertured layer to the film layer. Suitably, the backing sheet according to the present invention consists essentially of the film layer and the apertured adhesive-coated layer.

The solid substrate layer may for example be an apertured textile material, which may be woven or nonwoven, such as a gauze or an apertured nonwoven textile scrim. Suitable lightweight nonwovens are spunbonded webs or lightweight woven scrims such as those used in swabs.

In other embodiments the solid substrate layer may be a unitary thermoplastic layer, for example a network formed for example by extrusion or molding, or a perforated film produced for example by perforation of continuous films. Suitable substrates of this type include extruded films supplied by Smith and Nephew (CB15, CE15, SN09, H514, H518, H624 and PT20 all of which are Polyethylene except for PT20, which is Polypropylene). Also suitable are the apertured films and extruded nets from Delstar Inc. available under the Registered Trade Marks DELNET and NALTEX. The percent open area of the apertures in the apertured substrate layer is may be from about 1% to about 99%, for example from about 25% to about 90%, suitably from about 30% to about 80%.

The medically acceptable adhesive may be a hydrogel adhesive, but suitably it does not comprise a hydrogel. Suitably, the pressure-sensitive adhesive may be based on acrylate ester copolymers, polyvinyl ethyl ether and/or polyurethane. Polyurethane-based pressure sensitive adhesives are preferred. Pressure sensitive adhesives typically comprise an elastomer dissolved or dispersed in a non-aqueous solvent. Suitable pressure-sensitive adhesives are the polyurethane adhesives available under the registered trade mark LEVGEL. Also suitable are silicone-based adhesives available from Dow Corning. The adhesive may be applied to the apertured solid substrate layer via any method known on the art. The adhesive may be dissolved or dispersed in a suitable solvent prior to coating onto the substrate. The coated substrate may be squeezed, for example between rollers, after dipping in a bath of the adhesive (and optional solvent) to remove excess adhesive. The rollers may be profiled to provide the adhesive-free apertures in the substrate. The basis weight of the adhesive is regulated by the choice of substrate material, the concentration and viscosity of the adhesive bath in which the network is dipped, and the compression conditions after dipping. Suitably, the basis weight of the adhesive is less than about 100 gsm, for example from about 25 to about 75 gsm. The percent open (adhesive-free) area of the apertures in the adhesive-coated apertured layer is typically from about 1% to about 90%, for example from about 10% to about 60%, suitably from about 25% to about 75%.

In one embodiment, the adhesive backing sheets of the invention will have a moisture vapor transmission rate (MVTR) of about 300 to about 5000 $g/m^2/24$ hrs, for example about 500 to about 2000 $g/m^2/24$ hrs at 37.5° C. at 100% to 10% relative humidity difference and 32° C. by ASTM Standard E96-80. It has been found that such moisture vapor transmission rates allow the wound under the dressing to heal under moist conditions without causing the skin surrounding the wound to macerate.

Suitably, the maximum uncompressed thickness of the backing sheet according to the invention is from about 0.1 mm to about 2 mm, suitably from about 0.2 mm to about 1 mm.

The wound dressing according to the second aspect of the invention may comprise, consist essentially of, and/or consist of the backing sheet according to the invention, optionally with a protective cover sheet covering the surface of the adhesive-coated apertured layer opposite the continuous semipermeable film.

More usually, the wound dressing according to the invention further comprises a wound contacting sheet laminated to at least a region of the surface of the adhesive-coated apertured layer opposite the continuous semipermeable film. Suitably, the dressing is an island dressing, whereby an adhesive margin of the backing sheet extends around the wound contacting sheet. The width of the adhesive margin is suitably from about 5 mm to about 30 mm, for example from about 10 mm to about 20 mm. The width of the margin may be uniform, or it may vary in width, for example the wound contacting sheet may not be centered on the adhesive backing sheet.

The wound contacting sheet may be made up of one or more layers, usually including at least one absorbent layer. The absorbent layer may be any of the layers conventionally used for absorbing wound fluids, serum or blood in the wound healing art, including hydrophilic foams, gauzes, nonwoven fabrics, superabsorbents, hydro gels and mixtures thereof. The basis weight of the absorbent layer may be in the range of about 50 to about 500 g/m2, such as about 100 to about 400 glm$^2$. The uncompressed thickness of the absorbent layer may be in the range of from about 0.5 mm to about 10 mm, such as about 1 mm to about 4 mm. The free (uncompressed) liquid absorbency measured for physiological saline may be in the range of about 5 to about 30 g/g at 25° C.

Other optional layers of the wound contacting sheet include a liquid-permeable, non-adherent wound contacting (top) layer. One or more of the layers may contain one or more therapeutic agents such as humectants, antimicrobials (e.g. silver as metal or a silver salt), odor-absorbents (e.g. activated charcoal), and therapeutic agents to promote wound healing (e.g. growth factors, protease inhibitors).

The wound facing surface of the dressing is suitably protected by a removable cover sheet. The cover sheet is typically formed from flexible thermoplastic material. Suitable materials include but are not limited to polyesters and polyolefins. Suitably, the adhesive-facing surface of the cover sheet is a release surface. That is to say, a surface that is only weakly adherent to the adhesive on the backing sheet to assist peeling of the adhesive layer from the cover sheet. For example, the cover sheet may be formed from a non-adherent plastic such as a fluoropolymer, or it may be provided with a release coating such as a silicone or fluoropolymer release coating.

The area of the dressing according to this aspect of the invention may vary according to the type and size of wound, but is typically from about 1 cm$^2$ to about 500 cm$^2$, for example from about 4 cm-to about 100 cm.

Typically, the wound dressing according to the present invention is sterile and packaged in a microorganism-impermeable container. For example, sterilization may be performed by gamma-irradiation after packaging.

The method according to the present invention comprises: coating an apertured solid substrate with a medically acceptable adhesive to form an adhesive-coated apertured layer, followed by laminating the coated apertured layer to a semipermeable continuous film. Suitably, the method is adapted for the manufacture of an adhesive backing sheet according to the invention as defined above. Accordingly, all features described III relation to the first aspect of the invention are applicable to this aspect.

According to the present invention, the apertured layer may be coated for example by spraying or dipping the apertured layer with the adhesive, or with a solution or dispersion of the adhesive in a suitable solvent, followed by drying for example at temperatures of about 25° C. to about 100° C. Suitably, the adhesive-coated apertured layer is then compressed, for example between rollers, to remove excess adhesive.

Suitably, the method is performed substantially continuously on continuous webs of the apertured and backing film, followed by cutting the laminate into lengths.

An embodiment of the present invention will now be described further, by way of example, with reference to the accompanying drawings.

FIG. 1 shows a detail view of part of a backing sheet according to the invention;

Referring to FIG. 1, the wound dressing 1 is an island-type, self-adhesive wound dressing comprising an adhesive backing sheet 2 according to the present invention as described below. The backing sheet 2 is permeable to water vapor, but impermeable to wound exudates and microorganisms.

A wound contacting sheet 3, such as one comprised of absorbent polyurethane foam material of the kind described in EP-A-0541391 and available from Johnson & Johnson Medical Ltd. under the registered trade mark TIELLE, is adhered to a central region of the adhesive-coated backing sheet 2 such that an adhesive-coated margin 6 of the backing sheet extends around the island 2 for attachment of the dressing to the skin around a wound.

Figure 3:
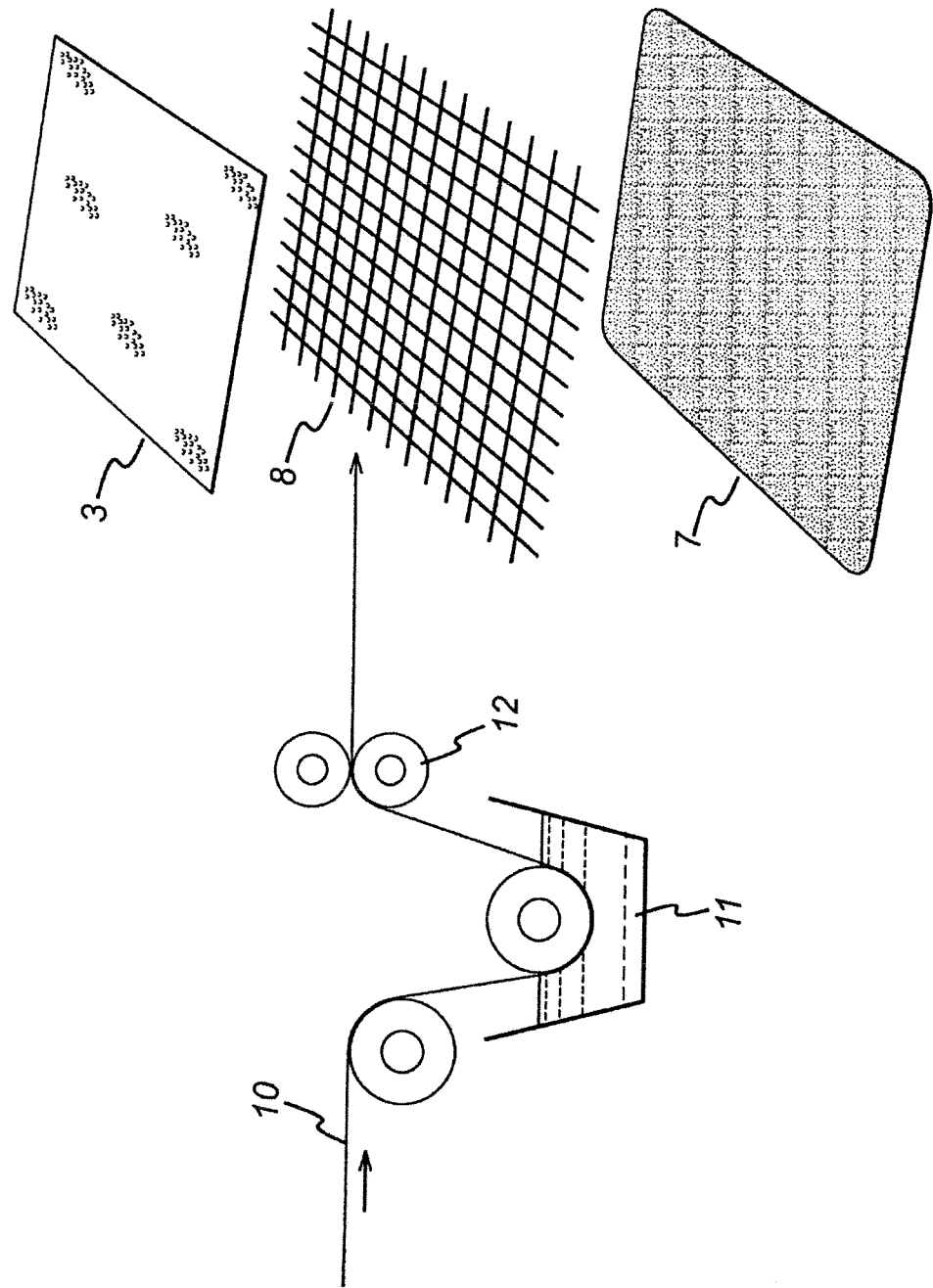
FIG. 3 shows a schematic view of a manufacturing process according to the invention.

Protective release-coated cover sheets 4,5 are provided as shown in FIG. 3. These cover sheets are removed immediately before use of the dressing.

Figure 2:
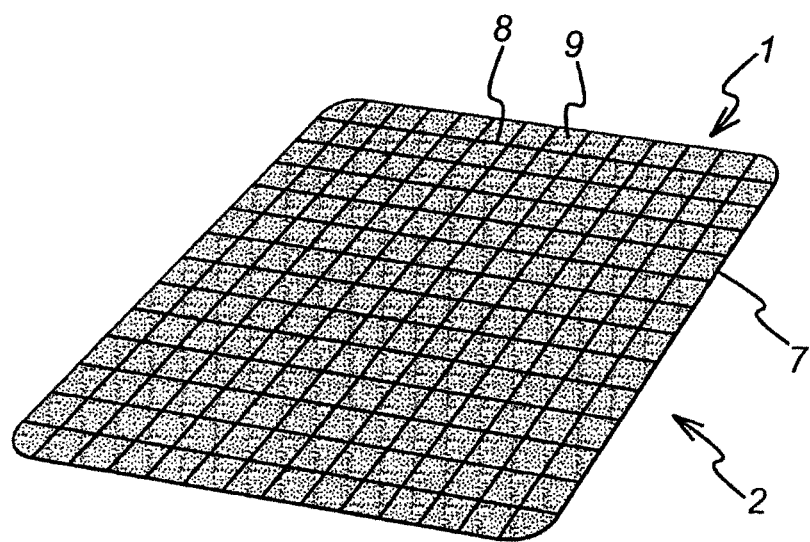
FIG. 2 shows a perspective view of a wound dressing according to the invention.

Referring to FIG. 2, the adhesive-coated backing sheet 2 comprises a continuous, thin, semipermeable polymer film 7 having laminated thereto an adhesive-coated apertured thermoplastic web 8. The strands of the apertured web 8 are coated with a pressure-sensitive, medically acceptable adhesive to bond the apertured web 8 to the polymer film 7, and also to provide the desired adherency and stiffness to the backing sheet 2.

Adhesive-free interstices 9 in the apertured web 8 provide the desired moisture- and oxygen-permeability to the backing sheet.

Referring to FIG. 3, one embodiment of the process according to the invention comprises dipping a continuous strip of apertured material 10 in a bath 11 of adhesive, followed by compression between rollers 12 to remove excess adhesive and laminating the coated 5 apertured 8 to the continuous film 7 and the wound contacting island 3.

The entire contents of the patent publications identified above are expressly incorporated herein by reference.

Many other embodiments of the present invention falling within the scope of the accompanying claims will be apparent to the skilled reader.

The invention claimed is:

1. A wound dressing, comprising:
   a backing sheet; and
   a wound contacting sheet comprising at least one absorbent layer;
   wherein the backing sheet comprises an apertured layer and a continuous film laminated to the apertured layer, the film being impermeable to wound exudates and to microorganisms and permeable to water vapor;
   wherein the apertured layer comprises an apertured substrate coated with a medically acceptable adhesive; and
   wherein the apertured layer is laminted between the wound contacting sheet and the continuous film.

2. A wound dressing according to claim 1, wherein a basis weight of the adhesive is from 25 to 75 gsm.

3. A wound dressing according to claim 1, wherein the continuous film has a thickness of from 20 micrometers to 75 micrometers.

4. A wound dressing according to claim 1 which is sterile, and packaged in a microorganism-impermeable container.

5. The wound dressing of claim 1, wherein the apertured substrate further comprises a thermoplastic net.

6. The wound dressing of claim 1, wherein a percent open area of the apertured layer is from 10% to 60%.

7. The wound dressing of claim 1, wherein the apertured layer comprises apertures adapted to allow passage of gas.

8. A method of making a backing sheet, comprising:
   forming an apertured layer by coating a medically acceptable adhesive onto an apertured substrate; and
   laminating the apertured layer between a continuous film and a wound contacting sheet comprising at least one absorbent layer;
   wherein the continuous film is permeable to water vapor, but impermeable to wound exudates and microorganisms.

9. The method of claim 8 wherein coating is carried out by spraying or dipping followed by passing between rollers to remove excess adhesive.

10. The method of claim 8 further comprising applying a removable cover sheet to the wound contacting sheet.

11. The method of claim 8, wherein a basis weight of the adhesive is from 25 to 75 gsm.

12. The method of claim 8, wherein the apertured substrate comprises a unitary thermoplastic net.

13. The method of claim 8, wherein the continuous film has a thickness of from 20 micrometers to 75 micrometers.

* * * * *